(12) United States Patent
Karavas et al.

(10) Patent No.: US 9,675,551 B2
(45) Date of Patent: Jun. 13, 2017

(54) SUBLINGUAL PHARMACEUTICAL COMPOSITION CONTAINING AN ANTIHISTAMINE AGENT AND METHOD FOR THE PREPARATION THEREOF

(75) Inventors: Evangelos Karavas, Pallini Attikis (GR); Efthimios Koutris, Pallini Attikis (GR); Vicky Samara, Pallini Attikis (GR); Amalia Diakidou, Pallini Attikis (GR); Aggelos Karatzas, Pallini Attikis (GR)

(73) Assignee: EXPERMED S.A., Kifisia Attikis (GR)

( * ) Notice: Subject to any disclaimer, the term of this patent is extended or adjusted under 35 U.S.C. 154(b) by 0 days.

(21) Appl. No.: 14/353,074

(22) PCT Filed: Oct. 25, 2011

(86) PCT No.: PCT/EP2011/005374
§ 371 (c)(1),
(2), (4) Date: Apr. 21, 2014

(87) PCT Pub. No.: WO2013/060343
PCT Pub. Date: May 2, 2013

(65) Prior Publication Data
US 2014/0235656 A1    Aug. 21, 2014

(51) Int. Cl.
A61K 9/00 (2006.01)
A61K 9/20 (2006.01)
A61K 31/522 (2006.01)
A61K 31/138 (2006.01)

(52) U.S. Cl.
CPC ............ *A61K 9/006* (2013.01); *A61K 9/2018* (2013.01); *A61K 9/2027* (2013.01); *A61K 9/2054* (2013.01); *A61K 9/2059* (2013.01); *A61K 9/2095* (2013.01); *A61K 31/138* (2013.01); *A61K 31/522* (2013.01)

(58) Field of Classification Search
IPC ................................ A61K 9/00,9/20, 31/522
See application file for complete search history.

(56) References Cited

U.S. PATENT DOCUMENTS

| | | | | |
|---|---|---|---|---|
| 6,127,385 A * | 10/2000 | Midha | | A61K 31/445 514/315 |
| 6,372,253 B1 * | 4/2002 | Daggy | | A61K 9/0056 424/464 |
| 7,229,980 B2 * | 6/2007 | Lee et al. | | 514/171 |
| 2007/0092553 A1 * | 4/2007 | Tengler | | A61K 9/0056 424/440 |
| 2008/0305166 A1 * | 12/2008 | Durig | | A61K 9/0056 424/464 |
| 2009/0004254 A1 * | 1/2009 | Maibach | | 424/444 |
| 2010/0215730 A1 * | 8/2010 | Guy | | A61K 9/0043 424/450 |
| 2010/0240631 A1 * | 9/2010 | Bellorini | | A61K 9/0007 514/177 |

FOREIGN PATENT DOCUMENTS

| | | |
|---|---|---|
| IT | WO9515155 A1 | 6/1995 |
| TR | WO2011024029 A1 | 3/2011 |
| WO | WO 95/15155 * | 6/1995 |
| WO | WO 2009078034 * | 6/2009 |

OTHER PUBLICATIONS

Patel et al. (Int.J. PharmTech Res.2009,1(3); 783-789).*
Scavone et al. (Biopharmaceutics & Drug Disposition, vol. 11, 185-189 (1990)).*
Joseph M. Scavone et al. Diphenhydramine kinetics following intravenous, oral and sublingual dimenhydrinate administration Biopharmaceutics&Drug Disposition, vol. 11, No. 3, Apr. 1, 1990 pp. 185-189.

* cited by examiner

*Primary Examiner* — Shirley V Gembeh
(74) *Attorney, Agent, or Firm* — AKC PATENTS, LLC; Aliki K. Collins

(57) ABSTRACT

The present invention relates to a stable pharmaceutical composition for sublingual administration comprising a therapeutically effective quantity of an antihistamine agent, in particular Dimenhydrinate and a process for the preparation thereof.

4 Claims, No Drawings

SUBLINGUAL PHARMACEUTICAL COMPOSITION CONTAINING AN ANTIHISTAMINE AGENT AND METHOD FOR THE PREPARATION THEREOF

TECHNICAL FIELD OF THE INVENTION

The present invention relates to a pharmaceutical formulation for sublingual administration comprising a therapeutically effective quantity of an antihistamine agent such as Dimenhydrinate or a pharmaceutical acceptable salt, derivative or polymorph thereof and a method for the preparation thereof.

BACKGROUND OF THE INVENTION

Antihistamines are drugs that block the action of histamine (a compound released in allergic inflammatory reactions) at the $H_1$ receptor sites. They are responsible for immediate hypersensitivity reactions such as sneezing and itching. Members of this class of drugs may also be used for their side effects, including sedation and antiemesis (prevention of nausea and vomiting). Antihistamines provide their primary action by blocking histamine $H_1$ at the receptor site. They have no effect on rate of histamine release, nor do they inactivate histamine.

Dimenhydrinate is primarily an ethanolamine-class antihistamine drug, i.e. a H1 antagonist but it possesses an antimuscarinic effect as well. Due to its antiemetic properties it is used to prevent the symptoms of motion sickness, vertigo, nausea after surgery and morning sickness during pregnancy. Moreover, it can be beneficial in vestibular disturbances and other types of true vertigo. Diphenhydrimine has also been used to reverse the extrapyramidal side effects caused by phenothiazines. One of the main characteristics of this compound is its pronounced tendency to induce sedation.

Chemically, Dimenhydrinate is a salt of two drugs, namely diphenhydramine and 8-chlorotheophylline which is a chlorinated derivative of the theophylline. Theophylline is very closely related to caffeine and theobromine, mild central nervous system stimulants. It was thought that by combining the antiemetic effects of diphenhydramine with a stimulant, the extreme drowsiness induced by the former could be mitigated somewhat by the latter. The sedation caused by diphenhydramine, however, is substantially stronger than the stimulation caused by chlorotheophyllinate, so the overall effect is still mostly sedating.

Dimenhydrinate has the empirical formula $C_{24}H_{28}ClN_5O_3$ representing a molecular weight of 469.96 [g/mol]. The chemical designation is 2-benzhydryloxy-N,N-dimethylethanamine compound with 8-chloro-1,3-dimethyl-7H-purine-2,6-dione. It is a white crystalline, odourless powder. It is freely soluble in ethanol, sparingly soluble in ethyl ether and slightly soluble in water.

The marketed product of Dimenhydrinate is available in the form of syrup, suppositories, capsules, film-coated tablets, chewable tablets and liquid.

In 1989 a study has been carried out in order to evaluate the possible use of the sublingual dosage route in the case of Dimenhydrinate. Said study compared the diphenhydramine kinetics after various route of administration, namely oral, sublingual and intravenous administration and the results of the study conveyed that systemic drug availability after sublingual administration was similar to that following oral administration on an empty stomach.

Various methods are already known for the industrial preparation of oral dosage forms comprising an antihistamine agent such as Dimenhydrinate as an active ingredient due to its useful therapeutical properties.

EP 1 219 291 B1 relates to a texture masked particle comprised of a core containing a bitter compound, such as Dimenhydrinate, a first layer of a taste masking agent and a second layer on the surface of the first layer containing a film forming polymer and an anti-grit agent. Chewable tablets made from these coated particles have good taste and exhibit an immediate release profile.

WO 2007/041367 A1 refers to an oral composition comprising Dimenhydrinate and a salivation inducing agent such as muscarinic acetylcholine receptor agonists, cholinesterase inhibitors, N,N-disubstituted phenalkylamines Saliva production is increased during ingestion, improving therefore the swallowability of such dosage forms. The dosage form is selected among chewable tablet, thin film strip, foam tablet and gummy.

US-A-2006/127479 discloses a taste masked pharmaceutical composition comprising a bitter tasting drug such as Dimenhydrinate prepared without using an organic solvent. Organic solvents have various effects on human health and may also pose a safety risk in the workplace.

Although each of the above patents represents an attempt to provide a pharmaceuticals compositions comprising Dimenhydrinate easy to swallow and thus accessible to patients with swallowing difficulties, there still exists a need for a sublingual tablet, particularly beneficial in patients who are unable to tolerate swallowing and in case of emergences due to the rapid absorption and onset of action.

SUMMARY OF THE INVENTION

It is, therefore, an object of the present invention to provide a sublingual pharmaceutical composition containing Dimenhydrinate or a pharmaceutical acceptable salt, derivative or polymorph thereof, which overcomes the deficiencies of the prior art with increased patient compliance and absorption rate of the drug via the blood vessels under the tongue.

It is another object of the present invention to provide a solid pharmaceutical dosage formulation for sublingual administration containing a Dimenhydrinate or a pharmaceutical acceptable salt, derivative or polymorph thereof, as an active ingredient, having an increased chemical stability of the active ingredient, sufficient self-life and good pharmacotechnical properties.

Moreover, it is another object of the present invention to provide a solid pharmaceutical dosage composition for sublingual administration containing a Dimenhydrinate or a pharmaceutical acceptable salt, derivative or polymorph thereof, as an active ingredient, which disintegrates fast without leaving an unpleasant taste in the mouth and which show a good physicochemical stability and low friability rendering them suitable for normal packaging and storing procedures.

The main objective of the present invention is to provide a quick-release formulation, capable of delivering the drug directly to the blood circulation and also capable of achieving rapidly the maximum drug levels in the plasma.

A further aspect of the present invention is to provide a method for the preparation of a stable solid dosage formulation for sublingual administration containing Dimenhydrinate or a pharmaceutical acceptable salt, derivative or polymorph thereof, as an active ingredient, which disintegrates fast without leaving an unpleasant taste in the mouth, thereby improving the pharmacotechnical characteristics of the composition and prepared in a simple and cost efficient manner.

In accordance with the above objects of the present invention, a pharmaceutical composition for oral administration is provided comprising an ethanolamine-class antihistamine drug such as Dimenhydrinate or a pharmaceutical acceptable salt, derivative or polymorph thereof, as an active ingredient and an effective amount of a pH dependent excipient as a taste masking agent, wherein said excipient is insoluble in acidic environment and soluble in neutral or alkaline conditions.

According to another embodiment of the present invention, a process for the preparation of solid dosage form for sublingual administration containing ethanolamine-class antihistamine drug such as Dimenhydrinate or a pharmaceutical acceptable salt, derivative or polymorph thereof, as an active ingredient and an effective amount of a pH dependent excipient as a taste masking agent, wherein said excipient is insoluble in acidic environment and soluble in neutral or alkaline conditions is provided, which comprises:

Blending Dimenhydrinate with the effective amount of a pH dependent excipient as a taste masking agent, at least one diluent, at least one glidant and at least one flavour enhancing agent until complete homogeneity.

Kneading the above mixture with a solvent and mixing until uniformity.

Drying the wetted mass.

Sieving the dried mass and adding to the sieved mixture, a disintegrant and mixing until uniform.

Adding to the obtained mixture, at least one lubricant and mixing until uniformity is achieved.

formulating the resulting mixture in a sublingual solid dosage form by compressing it into a desired tablet form.

Optionally, applying a coating.

Further preferred embodiments of the present invention are defined in dependent claims 2 to 10, and 12 to 14.

Other objects and advantages of the present invention will become apparent to those skilled in the art in view of the following detailed description.

DETAILED DESCRIPTION OF THE INVENTION

For the purposes of the present invention, a pharmaceutical composition comprising an active ingredient having an unpleasant taste (ethanolamine-class antihistamine drug such as Dimenhydrinate or salts thereof) is considered to be an active ingredient having taste characteristics which, when administered orally without any excipients, render the active ingredient unpalatable to a subject.

Further, the term "orally disintegrating", used in the present invention, means that the pharmaceutical composition disintegrates in less than 90 seconds as measured by the in vitro disintegration test according to Ph.Eur. The composition according to the present invention preferably disintegrates in less than 60 seconds.

The active ingredient (ethanolamine-class antihistamine drug such as Dimenhydrinate or salts thereof) contained in a dosage form is "bioavailable", if when administered in a dosage form is released from the dosage form, absorbed and reaches, at least the same, concentration levels in plasma as any of the marketed products containing the same quantity of the same active ingredient and intended for the same use.

Sublingual tablets are designed to dissolve in small quantity of saliva. After the tablet is placed in the mouth below the tongue, the patient should avoid eating, drinking and possibly talking in order to keep the tablet in place and avoid swallowing of saliva since the saliva may contain dissolved drug.

The main object of the present invention is to provide a quick-release composition. One of the main advantages of the sublingual administration is the fact that it circumvents exposure of drugs to digestive enzymes in the gastrointestinal tract and avoids the first pass effect from hepatic enzymes immediately upon absorption. The direct access to blood circulation in addition to the avoidance of any metabolism of the drug results in achieving quickly the maximum levels of the active ingredient in the plasma. Thus, a faster onset of pharmacological effects of the drug in patients is achieved in comparison to conventional oral delivery where the composition is swallowed.

The mucosa of the mouth is well vascularised and well suited for the absorption of lipophilic, nonionized compounds. The sublingual route is particularly beneficial for drugs which require a rapid onset of action. The sublingual tablets enable the administration of the drug by avoiding to be swallowed and also increase the absorption rate of the drug via the blood vessels under the tongue.

In addition, Dimenhydrinate has an unpleasant taste, such as bitter taste, causes numbness and contraction and the oral administration of said drug puts a burden on a patient and lowers compliance. Further, compounds with unpleasant taste such as Dimenhydrinate stimulate saliva flow which leads to increased swallowing of the drug. In fact, Dimenhydrinate causes numbness to the oral cavity for a relatively long period of time of about 10 minutes.

Thus, the unpleasant taste of Dimenhydrinate needs to be masked in order to reduce the numbness occurring when the active ingredient contacts the mucous membrane epithelium of the mouth.

The solid pharmaceutical composition for sublingual administration of the present invention is characterized by physicochemical properties suitable for a tablet formulation prepared by wet granulation, by adequate release rate of the active ingredient and storage stability achieved by employing excipients practically devoiding the tendency to interact with the active ingredient, and possessing good compressibility properties.

The excipients were chosen carefully to give appropriate dissolution rate and stability of the finished dosage form. The ultimate goal was to develop a stable immediate release formulation characterized by good taste and rapid disintegration which leads to greater absorption and high levels of the active ingredient in the systemic circulation.

It has been surprisingly found that the object of the present invention is achieved by employing an effective amount of a pH dependent excipient as a taste masking agent, that is insoluble in acidic environment and soluble in neutral or alkaline conditions, in order to reduce the numbness of the mucosa occurring when Dimenhydrinate contacts the mucosa, such as tongue and mouth mucosa.

Taste masking agents are selected from amberlite, Opadry® AMB TAN, polymethacrylates (especially Eudragit® L100), sodium starch glycolate (Primojel), carbopol polymers, PEG-5M, sodium acetate, ethylcellulose, betacyclodextrin, polyvinyl acetate dispersion, trehalose, vinylacetate, polystyrene, cellulose acetate butyrate.

According to the present invention anionic copolymers based on methacrylic acid and methyl methacrylates such as Eudragit® L100 are particularly useful in masking the taste but even more eliminating the numbness caused by the sublingual administration of Dimenhydrinate.

Eudragit® L100 is an excipient that dissolves on pH values above 6; therefore it is usually applied as an enteric coating that has fast dissolution in the upper bowel or intragranularly to control the release of the active substance from an oral tablet composition.

The present invention discloses a sublingual tablet formulation. Mixing Eudragit® L100 intragranularly with Dimenhydrinate results in the formation of a complex between the two based on hydrogen bonding interaction of the NH— groups of the active substance and the CO— groups of the polymer. The sublingual dosage form when placed in the oral cavity, in an environment of pH value of about 6 to 7, disintegrates quickly but the formed complex eliminates the numbness feeling that would appear if the active substance was alone. The mucoadhesive properties Eudragit® L100 further enhances the delivery of the active substance through erosion of the complex to the site of action i.e. the sublingual venous.

Furthermore, it has been found that when a super disintegrant such as sodium starch glycolate, also called Primojel, as a dissolution enhancing agent is incorporated in a pharmaceutical composition according to the present invention, disintegration properties of the sublingual dosage form are improved.

Sodium starch glycolate, a representative example of a cross-linked starch, is a modified starch possessing very significant disintegrating properties, and is practically insoluble in organic solvents. Chemically, Primojel constitutes a low substituted carboxy methyl starch. Sodium starch glycolate presents very good hydration capacity and very good flow properties in comparison to other super disintegrants. Further, it presents the tendency to absorb water rapidly, so it swells in a significant amount.

Therefore, this rapid water absorption by sodium starch glycolate molecules has as a result a significant increase in the volume of granules resulting to rapid and uniform disintegration. Sodium starch glycolate incorporated in a pharmaceutical composition facilitates the breakup or disintegration of the content of the tablet into smaller particles that dissolve more rapidly than in the absence of disintegrating agents. Sodium starch glycolate is incorporated into the composition of the present invention by external addition (extragranular).

The effective amount of taste masking agents has been optimized in order to obtain the maximum disintegration efficiency while reducing or eliminating numbness.

It has been found that the amount of the taste masking agent should be from about 10% to about 30% of the uncoated composition and preferably about 25% in order to improve the numbness. The amount of the disintegrant should be from about 5% to about 20% of the uncoated composition, and preferably about 14% of Primojel in order to aid taste masking, resulting in reduced numbness.

Additional excipients may be incorporate in the formulation in order to improve the physicochemical properties of the composition. Other flavour enhancers such as menthol, saccharin or vanilla may also be used in order to improve the taste of the tablets, limit the bitterness, and enhance the sweetness and the mouth feeling of the formulation.

Moreover, the pharmaceutical compositions of the present invention may also contain one or more additional formulation excipient such as diluents, disintegrants, binders, lubricants, glidants and flavouring agents, provided that they are compatible with the active ingredient of the composition, so that it does not interfere with it in the composition and in order to increase the stability of the drug and the self-life of the pharmaceutical product.

Diluents may be, for example, microcrystalline cellulose, dextrates, dextrose, fructose, mannitol, sorbitol, starch, pregelatinized starch, sucrose, xylitol, maltose, maltodextrin, maltitol. Disintegrants may be selected from alginic acid, carbon dioxide, carboxymethylcellulose calcium, carboxymethylcellulose sodium, croscarmellose sodium, guar gum, methylcellulose, polacrilin potassium, poloxamer, sodium alginate.

Binders may be, for example, alginic acid, carbomer, ethyl cellulose, gelatine, liquid glucose, guar gum, hydroxyethyl cellulose, methylcellulose, polydextrose, polyethylene oxide.

Also, at least a lubricant is incorporated into the formulation to prevent the powder from adhering to tablet punches during the compression procedure. Lubricants may be, for example, talc, magnesium stearate, calcium stearate, glyceryl behenate, hydrogenated castor oil, stearic acid, sodium lauryl sulphate.

Glidants are used to promote powder flow by reducing interparticle friction and cohesion. These are used in combination with lubricants as they have no ability to reduce die wall friction. Glidants, may be, for example, colloidal silicon dioxide, calcium silicate, calcium phosphate tribasic.

Flavouring agents are used to mask potential unpleasant tasting active ingredients and improve the likelihood that the patient will complete a course of medication. Such agents are particularly useful in case of orodispersible, chewable and sublingual tablets. Flavouring agents may be, for example, mint powder, menthol, vanillin, aspartame, acesulfame potassium, saccharin.

Another embodiment of the present invention is the use of the wet granulation process for the preparation of sublingual dosage forms of the present invention containing Dimenhydrinate or salts thereof, which is one of the most economical methods. Wet granulation is used mainly to improve flow and compressibility of powders and to prevent segregation of the blend components. It is used to convert a powder mixture into granules having suitable flow and cohesive properties for tabletting. The wet granulation process was preferred to other common manufacturing processes because it improves the hardness of the tablets by reducing friability. Said wet granulation process comprises:

Blending the total amount of the active ingredient (Dimenhydrinate or salts thereof) with the effective amount of a pH dependent excipient as a taste masking agent such as Eudragit® L100, at least one diluent such as microcrystalline cellulose or spray dried mannitol, at least one glidant such as colloidal silica anhydrous and at least one flavour enhancing agent such as menthol or saccharin acid or vanilla until complete homogeneity.

Kneading the above mixture with a solvent such as ethanol and mixing until uniformity.

Drying the wetted mass.

Sieving the dried mass and adding to the sieved mixture a disintegrant such as sodium starch glycolate and mixing until uniform.

Adding to the obtained mixture, at least one lubricant such as magnesium stearate or talc and mixing until uniformity is achieved.

formulating the resulting mixture in a sublingual solid dosage form by compressing it into a desired tablet form.

Optionally, applying a coating.

Sublingual tablets have to conform to some specifications as regard disintegration time, hardness and friability. They must also fulfil some other physical requirements i.e. having good rheological properties. The disintegration time of the tablet of the present invention is preferably 50-55 seconds, the crushing strength of the tablet is about 50N and friability is less than 0.3%. Finally, for the evaluation of the rheology of the powder, Carr's index is preferably about 18%, value which indicate good flowability.

The pharmaceutical compositions of the present invention are also characterized by excellent pharmacotechnical properties, such as homogeneity, flowability and compressibility. Thanks to these properties, the solid dosage forms prepared by the above process exhibit excellent technical characteristics including disintegration time, dissolution rate, hardness, resistance to crashing, friability and stability.

The following examples illustrate preferred embodiments in accordance with the present invention without limiting the scope or spirit of the invention

EXAMPLES

Example 1

TABLE 1

Formulation of Dimenhydrinate tablets of Example 1

| Ingredients | mg per tablet |
| --- | --- |
| Dimenhydrinate | 52.3 |
| Opadry ® AMB Tan solution 15% w/w | q.s. |
| Spray-dried Mannitol (Mannogem EZ) | 10 |
| Cellulose microcrystalline (Avicel PH302) | 40 |
| Kollidon 30 | 20 |
| Amberlite | 50 |
| Aspartame | 16.6 |
| Saccharin acid | 5 |
| Silica colloidal anhydrous (Aerosil) | 3 |
| Banana | 0.2 |
| Vanilla | 0.2 |
| Menthol | 3 |
| Total weight | 201.3 |

The sublingual tablets of the above formulation were prepared according to the following manufacturing process: Opadry® AMB Tan was dissolved into water and Dimenhydrinate was kneaded with said Opadry® AMB Tan solution that was used as a taste masking agent and in order to control numbness. The mixture was dried in an oven of about 35° C. The dried mass was sieved through a sieve and subsequently it was mixed with all the remaining excipients. The final mixture of powder was compressed into tablets.

The produced sublingual tablets were tested for hardness, friability and disintegration. The pharmacotechnical properties of the tablets were within the desirable level. The hardness of the tablets was about 50N, the disintegration time was below 1 min and the friability was less than 0.3%.

Amberlite has been used as a taste masking agent due to its taste masking properties, which reduced the bitter taste of the drug and Kollidon 30 has been used as a disintegrant.

The results of the dissolution profile of the sublingual tablets are shown in Table 2.

TABLE 2

Release of Dimenhydrinate tablets of Example 1

| Time (min) | % Dissolved |
| --- | --- |
| 5 | 75.50 |
| 10 | 100.1 |
| 15 | 104.21 |
| 20 | 107.61 |

TABLE 2-continued

Release of Dimenhydrinate tablets of Example 1

| Time (min) | % Dissolved |
| --- | --- |
| 25 | 108.51 |
| 30 | 108.83 |
| 40 | 108.35 |

The pharmacotechnical characteristics of the composition of Example 1 were satisfactory and the numbness was acceptable, however the stability analysis showed high impurity levels.

Example 2

TABLE 3

Formulation of Dimenhydrinate tablets of Example 2

| Ingredients | mg per tablet |
| --- | --- |
| Dimenhydrinate | 52.3 |
| Opadry ® AMB Tan solution 15% w/w | q.s. |
| Spray-dried Mannitol (Mannogem EZ) | 40 |
| Cellulose microcrystalline (Avicel PH302) | 40 |
| Sodium starch glycolate (Primojel) | 40 |
| Amberlite | 40 |
| Aspartame | 10 |
| Saccharin acid | 3 |
| Silica colloidal anhydrous (Aerosil) | 5 |
| Banana | 0.2 |
| Vanilla | 0.2 |
| Menthol | 3 |
| Magnesium stearate | 6 |
| Total | 239.7 |

The sublingual tablets of the formulation of Example 2 have been prepared following the same manufacturing process as in Example 1. In order to improve the stability of Example 1, sodium starch glycolate has been used as super disintegrant.

The hardness of the produced tablets was about 30N, the disintegration time was below 1 min and the friability was about 4%.

The results of the dissolution profile of the tablets are shown in Table 4.

TABLE 4

Release of Dimenhydrinate tablets of Example 2

| Time (min) | % Dissolved |
| --- | --- |
| 3 | 67.59 |
| 11 | 81.79 |
| 19 | 87.65 |
| 27 | 95.06 |
| 35 | 95.99 |
| 43 | 98.46 |

The sublingual tablets of the formulation of Example 2 had good taste and the problem of the numbness was eliminated due to the fact that Dimenhydrinate has been kneaded with Opadry® solution. However, the friability of the tablets was very high and the level of undesirable impurities was high.

Example 3

Further compatibility studies showed that even though Opadry® AMB Tan solution 15% w/w was effective for controlling numbness caused by the active ingredient, it was also responsible for the high impurities levels. Additionally, in order to improve the friability of the tablets a different manufacturing process has been followed.

TABLE 5

Formulation of Dimenhydrinate tablets of Example 3

| Ingredients | mg per tablet |
|---|---|
| Internal Phase | |
| Dimenhydrinate | 50 |
| Cellulose microcrystalline (Avicel PH302) | 20 |
| Sodium starch glycolate (Primojel) | 40 |
| Amberlite | 40 |
| Aspartame | 5 |
| Saccharin acid | 2 |
| Banana | 0.2 |
| External Phase | |
| Spray-dried Mannitol (Mannogem EZ) | 40 |
| Cellulose microcrystalline | 20 |
| Vanilla | 0.2 |
| Aspartame | 5 |
| Saccharin | 1 |
| Silica colloidal anhydrous (Aerosil) | 5 |
| Menthol | 3 |
| Magnesium stearate | 6 |
| Total | 237.4 |

The sublingual tablets of the formulation of Example 3 were prepared according to the following manufacturing process: Dimenhydrinate was mixed with all excipients of the internal phase and granulated with water. The wetted mass was then dried and passed through a sieve to achieve the desired granule size. The dried internal phase mixture was further mixed with the excipients of the external phase and the final mixture was compressed into sublingual tablets.

The pharmacotechnical properties of the sublingual tablets were within the desirable level. The hardness of the tablets was about 71N, the disintegration time was below 1 min and the friability was 0.5%.

The results of the dissolution profile of the tablets are shown in Table 6.

TABLE 6

Release of Dimenhydrinate tablets of Example 3

| Time (min) | % Dissolved |
|---|---|
| 3 | 77.36 |
| 11 | 92.85 |
| 19 | 96.13 |
| 27 | 96.94 |
| 35 | 97.65 |
| 43 | 99.51 |

In spite of the desired pharmacotechnical properties and the satisfactory dissolution profile, the numbness feeling was not satisfactory and the impurity levels were high.

Example 4

TABLE 7

Formulation of Dimenhydrinate tablets of Example 4

| Ingredients | mg per tablet |
|---|---|
| Internal phase | |
| Dimenhydrinate | 50 |
| Cellulose microcrystalline (Avicel PH302) | 85 |
| Spray-dried Mannitol (Mannogem EZ) | 20 |
| Sodium starch glycolate (Primojel) | 20 |
| Vanilla | 0.4 |
| Saccharin acid | 8 |
| Silica colloidal anhydrous (Aerosil) | 10 |
| Menthol | 3 |
| External phase | |
| Magnesium Stearate | 1 |
| Talc | 1 |
| Total weight | 198.4 |

The sublingual tablets of the formulation of Example 4 were prepared according to the following manufacturing process: Dimenhydrinate and all the excipients of the internal phase were mixed and kneaded with ethanol. The mixture was dried and sieved. To the resulted dried mixture all excipients of the external phase was added and mixed until homogeneity and subsequently compressed into sublingual tablets.

The pharmacotechnical properties of the tablets were within the desirable level. Disintegration was 40 sec, friability 0.01% and hardness was 97N.

The use of wet granulation process improved the cohesiveness of the sublingual tablets. Thus, it was used for the preparation of tablets of Example 4 with the difference that ethanol was used as the granulation liquid.

The stability results of formulation of Example 4 were significantly improved compared to the other formulation trials. However, the numbness issue was still present.

Example 5

TABLE 8

Formulation of Dimenhydrinate tablets of Example 5

| Ingredients | mg per tablet |
|---|---|
| Internal phase | |
| Dimenhydrinate | 50.0 |
| Methacrylic acid - methyl methacrylate copolymer (Eudragit ® L100) | 48.0 |
| Cellulose microcrystalline (Avicel PH302) | 34.0 |
| Spray-dried Mannitol (Mannogem EZ) | 13.0 |
| Vanilla | 0.4 |
| Saccharin acid | 9.4 |
| Silica colloidal anhydrous (Aerosil) | 12.0 |
| Menthol | 2.0 |
| External phase | |
| Sodium starch glycolate (Primojel) | 28.0 |
| Magnesium Stearate | 0.8 |
| Talc | 0.8 |
| Total weight | 198.4 |

A wet granulation process was used for the preparation of the sublingual tablets of Example 5 according to the following manufacturing process: Dimenhydrinate and all the excipients of the internal phase were mixed until complete homogeneity. The obtained mixture was kneaded using ethanol absolute (99.9%) as solvent. The wetted mass was dried. Sodium starch glycolate was added to the dried mixture and further mixed until uniform. The total amount of talc and magnesium stearate were added to the above mixture and blended. Subsequently, the resulted mixture compressed into sublingual tablets. Optionally, a coating may be applied.

In order to improve the numbness feeling Eudragit® L100 was used as a taste masking agent and the results were very satisfactory.

The pharmacotechnical properties of the sublingual tablets of Example 5 were within the desirable level and the stability data were improved. The in vivo study proved that the sublingual dosage form of the present invention was bioequivalent to the marketed product.

The pharmaceutical compositions of the present invention have been tested in view of the taste masking efficiency. The test was carried out by 6 healthy volunteers holding sublingual tablets for examination in their mouth, and then evaluated the degree of a bitter taste and numbness in accordance of three grades. The sublingual tablets were prepared in accordance to Example 1 to 5 of the present invention.

The sublingual tablets were left to disintegrate for 60 seconds in the oral cavity to disintegrate and then were thrown out. Then the mouth was washed with water.

The marking "+++" used in the test represents the highest degree of bitterness/numbness.

The results of this evaluation are shown in Table 9.

TABLE 9

| Results of the evaluation | | | | | |
| --- | --- | --- | --- | --- | --- |
| Taste | Example 1 | Example 2 | Example 3 | Example 4 | Example 5 |
| Bitterness | ++ | ++ | +++ | +++ | + |
| Numbness | ++ | ++ | +++ | +++ | + |

The advantage of the preferred sublingual composition according to Example 5 of the present invention in comparison to the commercially available Dimenhydrinate dosage forms is the immediate relief of nausea symptoms. Furthermore, it provides an excellent solution in the treatment of patients with acute vomiting symptoms, in the cases of which inadequate absorption of the drug after oral administration constitutes a problem.

While the present invention has been described with respect to the particular embodiments, it will be apparent to those skilled in the art that various changes and modifications may be made in the invention without departing from the spirit and scope thereof, as defined in the appended claims.

The invention claimed is:

1. A pharmaceutical composition in a form of a tablet for sublingual administration comprising Dimenhydrinate or a pharmaceutical acceptable salt thereof, an extragranular disintegrant and an effective amount of pH dependent excipient as a taste masking agent to reduce the numbness of the mucosa, wherein said excipient is insoluble in acidic environment and soluble in neutral or alkaline conditions;
   wherein the taste-masking agent that reduces the numbness of the mucosa is Poly(methacrylic acid-co-methyl methacrylate) 1:1;
   wherein the extragranular disintegrant is sodium starch glycolate; and
   wherein the taste-masking agent that reduces the numbness of the mucosa is from about 5 to about 50 wt % of the total weight of the composition.

2. The pharmaceutical composition according to claim 1, further comprising at least one pharmaceutically acceptable excipient selected from diluents, flavour enhancers, glidants, and lubricants.

3. The pharmaceutical composition according to claim 1, further comprising microcrystalline cellulose, spray-dried mannitol, sodium starch glycolate, vanilla flavour, saccharin acid, silica colloidal anhydrous, magnesium stearate, menthol and talc.

4. A process for the preparation of a tablet for sublingual administration comprising Dimenhydrinate or a pharmaceutical acceptable salt thereof, as the active ingredient, and an effective amount of a pH dependent excipient as a taste masking agent, to reduce the numbness of the mucosa, wherein said excipient is insoluble in acidic environment and soluble in neutral or alkaline conditions, and an extragranular disintegrant, wherein said process comprises:
   Blending the active ingredient with the pH dependent excipient and at least one pharmaceutically acceptable excipient selected from diluents, glidants, and flavour enhancers until complete homogeneity;
   Kneading the above mixture with ethanol and mixing until uniformity;
   Drying the wetted mass;
   Sieving the dried mass and adding to the sieved mixture, the extragranular disintegrant and mixing until uniform;
   Adding to the obtained mixture, at least one pharmaceutically acceptable excipient selected from glidants and lubricants and mixing until uniformity is achieved;
   Compressing the resulted mixture into a sublingual tablet dosage form;
   Optionally, applying a coating;
   wherein the taste-masking agent that reduces the numbness of the mucosa is Poly(methacrylic acid-co-methyl methacrylate) 1:1;
   wherein the extragranular disintegrant is sodium starch glycolate; and
   wherein the taste-masking agent that reduces the numbness of the mucosa is from about 5 to about 50 wt % of the total weight of the composition.

* * * * *